United States Patent [19]

Griffiths et al.

[11] 4,332,895

[45] Jun. 1, 1982

[54] THERMAL STABLE BETA-GALACTOSIDASE

[75] Inventors: Mansel W. Griffiths, Kilmarnock; David D. Muir, Irvine; John D. Phillips, Prestwick, all of Scotland

[73] Assignee: National Research Development Corp., London, England

[21] Appl. No.: 45,654

[22] Filed: Jun. 5, 1979

[30] Foreign Application Priority Data

Jun. 7, 1978 [GB] United Kingdom ............... 26503/78

[51] Int. Cl.³ .................... C12P 19/02; C12N 11/02; C12N 9/38
[52] U.S. Cl. ..................................... 435/105; 426/41; 435/174; 435/177; 435/179; 435/180; 435/207
[58] Field of Search ................. 435/94, 207, 105, 174, 435/177, 179, 180, 181; 426/41

[56] References Cited

U.S. PATENT DOCUMENTS

| | | | |
|---|---|---|---|
| 3,816,259 | 6/1974 | Collinge et al. | 435/207 |
| 3,852,496 | 12/1974 | Weetall et al. | 426/41 |
| 4,179,335 | 12/1979 | Long et al. | 435/207 X |

FOREIGN PATENT DOCUMENTS

1497459 1/1978 United Kingdom .
1531303 11/1978 United Kingdom .

OTHER PUBLICATIONS

Syrup: A New By—Product of Milk, Scottish Farmer, Nov. 22, 1977.
Jack et al., The Immobilization of Whole Cells, Advances in Biochem. Eng. vol. 5, 1977, (pp. 127-145).
Goodman et al., B—Galactosidase from *Bacillus Stearothermophilus,* Can. J. Microbiol. vol. 22, 1976, (pp. 817-825).
Ulrich et al., Induction and Characterization of B—Galactosidase in an Extreme Thermophile, J. of Microbiol., vol. 110, No. 2, 1972, (pp. 691-698).

*Primary Examiner*—David M. Naff
*Attorney, Agent, or Firm*—Oblon, Fisher, Spivak, McClelland & Maier

[57] ABSTRACT

A thermal stable beta-galactosidase enzyme is produced from new strains of *Bacillus stearothermophilus.* The beta-galactosidase is suitable for hydrolysis of lactose at temperatures of at least 55° C. and is especially suitable for use at temperatures of at least 65° C. For hydrolysis of lactose, the beta-galactosidase enzyme may be in the form of substantially purified enzyme that has been immobilized or immobilized whole cells containing beta-galactosidase enzyme.

9 Claims, 10 Drawing Figures

THERMAL STABLE BETA-GALACTOSIDASE

This invention relates to enzymes and processes utilising enzymes, in particular to β-galactosidase enzymes and their use in the enzymatic hydrolysis of lactose.

Lactose is the sugar component of whey, the liquid which remains after the separation of solids from milk or cream during customary cheese-making processes, and which at the present time is often regarded as a waste material and presents a disposal problem. In view of its low sweetness and solubility and tendency to undesirable crystallisation, lactose is unsatisfactory for use as a food sugar. Lactose, however, is a dimer of glucose and galactose and may be hydrolysed to its separate sugar units which are then readily utilisable as food sugars. Straightforward acid hydrolysis of lactose may be used, though this is not usually satisfactory because side reactions take place giving rise to a product having undesirable flavours. Alternatively hydrolysis may be effected by use of a β-galactosidase enzyme, although the temperature optimums for known β-galactosidase enzymes, i.e. from about 30°-40° C. up to a maximum of about 50° C., permit microbial growth which seriously contaminates the product.

New β-galactosidase enzymes have now been discovered which may be used for hydrolysis of lactose whilst avoiding the problem of contamination by adventitious microbial growth.

Accordingly, the present invention provides a novel β-galactosidase enzyme, said enzyme being of thermal stability such that it has an activity half life of at least 1½ hours at 55° C., at least 1 hour at 60° C. and at least 10 minutes at 65° C., as measured using ONPG as substrate, said enzyme being derived from a bacterium of species Bacillus stearothermophilus. The invention also includes enzyme compositions and enzymically active whole cell preparations of bacteria of species B. stearothermophilus which contain the novel β-galactosidase of the invention.

A useful indicator of the suitability of strains of Bacillus stearothermophilus for derivation of the β-galactosidase of the invention is ability to grow at elevated temperatures, usually at least 60° C. and preferably at least 65° C., utilising lactose as sole carbon source. A basal salts culture medium containing lactose may be used for growth of the bacterium e.g. a basal salts medium as hereinafter specifically described, and evidence of growth may be determined by methods well known in the art. Growth at elevated temperatures is only an indicator, however, and suitability is ultimately determined by the thermal stability and persistence of the β-galactosidase derived from the strain of B. stearothermphilus in question. For the purpose of the present description, the thermal stability of the enzyme is defined in terms of its activity half life, with respect to ONPG (orthonitrophenyl-β-D-galactopyranoside) as substrate, at various temperatures. Preferably, the thermal stability of the enzyme is such that it has an activity half life of at least 5 hours at 55° C., at least 3 hours at 60° C., at least 1 hour at 65° C., and especially also at least ten minutes at 70° C. The activity half lives given above are typically measured using purified enzyme extract. Whole cell preparations may exhibit slightly longer half life periods than purified enzyme extracts at the higher temperatures i.e. 65° and 70° C., used and typical activity half lives for whole cell preparations according to the invention are at least 45 minutes at 65° C. and at least 5 minutes at 70° C.

Preferred strains of B. stearothermophilus for derivation of the novel β-galactosidase, enzyme compositions and enzymically active whole cell preparations of the invention are represented by the related group of strains recently discovered by workers at the Hannah Research Institute (HRI), Ayr, Scotland. Cultures of these strains of B. stearothermophilus were deposited with the National Collection of Industrial Bacteria, Torry Research Station, Aberdeen, Scotland on the 24th of May 1978, and the deposits are identified by the reference numbers NCIB 11407, NCIB 11408, NCIB 11409, NCIB 11410, NCIB 11411, NCIB 11412 and NCIB 11413, which are hereinafter referred to as the HRI A/S 1, A/S 2, A/S 3, A/S 4, A/S 5, A/S 6 and A/S 8 strains respectively of B. stearothermophilus.

Preferred strains may also include variants and mutants of the HRI strains of B. stearothermophilus and such variants and mutants are new, and together with the HRI strains are included within the scope of the invention. The HRI strains have been derived from continuous cultures grown over a considerable period of time, preferably using lactose as sole carbon source, and it is believed that the HRI strains may have arisen as mutants and been preferentially selected during this culturing.

The HRI organisms have been identified as strains of B. stearothermophilus from the following characteristics: they are non-motile, rod-shaped (typically 0.6μ wide, 2.0μ long, from scanning electron micrographs), have a positive Gram stain and form spores. They are obligate aerobes, all hydrolyse urea, all but one hydrolyse casein and many also hydrolise starch. All produce acid from lactose, mannitol, sucrose and maltose, and all but one are insensitive to azide. The organisms do not appear to grow at 30° or 37° C., and have a minimum growth temperature of about 45° C. and a maximum growth temperature of about 65° C. Advantageously, also, the HRI strains of B. stearothermophilus are typically constitutive for β-galactosidase production, i.e. give rise to the β-galactosidase of the invention independent of the substrate on which the organisms are grown.

The characteristics of the various HRI strains of B. stearothermophilus given below in Table I characterise these organisms from other strains of B. stearothermophilus. It will be appreciated, however, that other strains of B. stearothermophilus, having the same or similar characteristics may be suitable for derivation of the novel β-galactosidases of the invention.

TABLE 1

| Strain | Characteristics of HRI strains of B. stearothermophilus | | | | | | | | |
| --- | --- | --- | --- | --- | --- | --- | --- | --- | --- |
| | HRI A/S 1 | HRI A/S 2 | HRI A/S 2B | HRI A/S 3 | HRI A/S 4 | HRI A/S 5 | HRI A/S 6 | HRI A/S 7 | HRI A/S 8 |
| Gram stain | + | + | + | + | + | + | + | + | + |
| Spores | ✓ | ✓ | ✓ | ✓ | ✓ | ✓ | ✓ | ✓ | ✓ |
| Motility | − | − | − | − | − | − | − | − | − |
| Catalase production | + | + | + | + | + | + | + | + | + |
| Temperature max. 65° | + | + | + | + | + | + | + | + | + |

TABLE 1-continued

| Strain | Characteristics of HRI strains of B. stearothermophilus | | | | | | | | |
|---|---|---|---|---|---|---|---|---|---|
| | HRI A/S 1 | HRI A/S 2 | HRI A/S 2B | HRI A/S 3 | HRI A/S 4 | HRI A/S 5 | HRI A/S 6 | HRI A/S 7 | HRI A/S 8 |
| min. 45° | + | + | + | + | + | + | + | + | + |
| 30° | − | − | − | − | − | − | − | − | − |
| Acid production from | | | | | | | | | |
| ARABINOSE | + | + | + | − | − | + | + | + | + |
| XYLOSE | + | + | + | − | − | + | + | + | + |
| MANNITOL | + | + | + | + | + | + | + | + | + |
| SUCROSE | + | + | + | + | + | + | + | + | + |
| LACTOSE | + | + | + | + | + | + | + | + | + |
| GLUCOSE | + | + | + | + | + | + | + | + | + |
| MALTOSE | + | + | + | + | + | + | + | + | + |
| Vosges-Proskaner | − | − | − | − | − | − | − | − | − |
| Growth on: | | | | | | | | | |
| 5% NaCl | + | + | + | + | + | + | + | + | − |
| 0.02% Azide | − | + | + | + | + | + | + | + | + |
| 0.001% Lysozyme | + | − | − | + | + | + | + | + | + |
| Decomposition of: | | | | | | | | | |
| Casein | + | + | + | − | + | + | + | + | + |
| Starch | + | + | + | − | − | − | + | + | + |
| Urea | + | + | + | + | + | + | + | + | + |
| Specific Activity of β-galactosidase from cells grown on nutrient broth (μmole/min/mg protein) at 65° C. | 0.09 | 0.36 | 0.13 | 0.10 | 0.05 | 0.35 | 4.61 | 3.23 | 4.07 |

All incubations done at 65° C. except where stated otherwise

The novel β-galactosidase enzyme systems of the invention, as derived from the HRI strains of B. stearothermophilus and variants and mutants thereof (those derived from the HRI strains of B. stearothermophilus being hereinafter termed the HRI enzyme), are typically distinguished from other β-galactosidases derived from prior art strains of B. stearothermophilus, such as the strain described by Goodman and Pedersen (Canadian Journal of Microbiology, 22 (1976), 817–825) by the following chracteristics:

1. The novel enzymes characteristically have significantly greater thermal stability. For instance, the purified HRI enzyme shows no change in activity after 90 minutes incubation at 55° C., an activity half life of 450 minutes after incubation at 60° C., an activity half life of 85 minutes after incubation at 65° C., and an activity half life of 20 minutes after incubation at 70° C., as assayed using ONPG as substrate at pH 7.0.

2. The novel enzymes typically have significantly greater affinity for substrates e.g. lactose and ONPG, than prior art enzymes. For example, the HRI enzyme has Michaelis constants (Km) of 0.43 mM and 2.1 mM for substrates ONPG and lactose respectively, as measured at 65° C.

3. The novel enzymes are typically activated by magnesium ion; the HRI enzyme being activated by 60% on addition of magnesium ion at a level of 10 mM.

4. The novel enzymes are generally significantly more active at acid pHs than prior art β-galactosidases. For example, the purified HRI enzyme has an activity maximum of a 100% at pH 6.0 and activities ranging from about 10% at pH 5 to 53% at pH 7.5.

These and various other characteristics will be hereinafter described in more detail with reference to the specific case of the HRI enzyme; although, without prejudice to the scope of the invention, it is believed that in general the enzymes of the invention will exhibit similar characteristics.

The enzyme, enzyme compositions and enzymatically active whole cell preparations of the invention are derived by first cultivating a culture of a suitable strain of B. stearothermophilus. Cultivation is typically carried out at elevated temperature, generally at least 60° C., preferably about 65° C., on a suitable culture medium, such as a basal salts culture medium, comprising lactose as sole carbon source. Any suitable cultivation regime may be employed including either batch or continuous culture. The purified enzyme or partially purified enzyme extracts and compositions comprising the enzyme are obtained by extraction of enzyme from the cells e.g. by lysing, followed by purification procedures as required. Purified enzyme or enzyme extracts may be immobilised on or with a suitable solid phase material such as an ion-exchange material e.g. DEAE-cellulose or like material, to provide preferred immobilised enzyme composition products.

Whole cell preparations may be subjected to preparative treatment to render the cells permeable, and thus enhance apparent enzyme activity for lactose hydrolysis. One treatment which may be used to render cells permeable is treatment with toluene, e.g. toluene—acetone solution. Permeable whole cell preparations may preferably be immobilised, for instance, in a gel matrix to provide an advantageously immobilised enzymatically active whole cell preparation. In particularly preferred embodiments, however, permeable whole cell preparations are immobilised with a suitable ion-exchange support material, including in particular DEAE-cellulose and like ion-exchange materials such as amino ethyl cellulose, DEAE-Sephadex and DEAE-Sepharose.

Preferred processes for production of immobilised enzyme composition products or especially immobilised whole cell products, immobilised with ion-exchange support materials, comprise prior treatment of the ion exchange material with glutaraldehyde or a similar linking reagent e.g. carbodiimides so as to covalently attach the enzyme or cells to the ion exchange support material. Such prior treatment, in particular with DEAE-cellulose and like ion-exchange support materials, advantageously gives products having greater retention of enzyme activity than products prepared without such prior treatment, and preferably also products of outstanding thermal stability. For example, whole cell products immobilised on DEAE-cellulose which has been pre-treated with glutaraldehyde often have activity half lives of at least 7 days, in some cases about 15 days, at 60° C. and pH 7.

The products of the invention may be used in processes for the hydrolysis of lactose to glucose and galactose.

Thus in a further aspect the invention includes a process for the hydrolysis of lactose to a product comprising glucose and galactose, in which lactose is contacted with a novel $\beta$-galactosidase enzyme, composition or enzymatically active whole cell preparation according to the invention. Typically the process is carried out at elevated temperature, usually at a temperature of at least 55° C., preferably at a temperature of at least 60° C., especially about 65° C. Generally the procedures and apparatus employed for hydrolysis of lactose are similar to those commonly used in equivalent or other enzymatic hydrolysis processes and a wide range of possible systems and procedures will be apparent to workers skilled in the art. Thus in a preferred embodiment, in a continuous incubation mode, substrate containing lactose in solution form is passed into a reactor containing the enzyme or enzymatically active whole cell preparation, preferably in immobilised form e.g. immobilised enzyme composition or immobilised whole cell preparation, and the glucose and galactose products are recovered downstream of the reactor.

Any suitable source of lactose may be used as the substrate in the process of the invention, for instance the lactose may be derived by purification from whey or other suitable source. Preferably, however, the crude whey itself or other lactose containing milk product is contacted directly with the enzyme, composition or enzymically active whole cell preparation, e.g. in a reactor. In this latter respect the use of the enzyme of the invention is particularly advantageous in view of the magnesium ion activation which it exhibits and the advantageous breadth of pH compatibility of the enzyme. Generally also, however, the use of the process of the present invention is particularly advantageous in that the elevated temperatures used, e.g. at least 55° C. and preferably at least 60° C., significantly diminish the risk of contamination by adventitious microbial growth. Furthermore, the strains of B. stearothermophilus used do not appear to grow at 37° C. and thus do not present a substantial contamination problem for the glucose/galactose product.

Moreover, in view of the desirable high thermal stability of the enzyme of the invention, the enzyme may be incorporated directly with UHT milk products prior to heat treatment and may be advantageously sterilised along with the milk during heat treatment and subsequently convert lactose contained therein to glucose and galactose.

The process of the invention provides a lactose hydrolysate product comprising glucose and galactose, and may be in partially or fully hydrolysed form. The hydrolysate may be concentrated to produce hydrolysate syrups which may find advantageous uses in the confectionery and brewing industries. Alternatively the glucose and/or galactose produced may be recovered in purified form and further utilised as required.

The invention is further described by way of illustration only in the following examples which refer to the accompanying diagrams, in which.

EXAMPLE 1.

Growth of bacterium *Bacillus stearothermophilus*

The basal salts medium used for batch and continuous culture of strains of *B. stearothermophilus* is as follows:

| | |
|---|---|
| nitrilotriacetic acid | 100 mg/l |
| Mg SO$_4$ 7 H$_2$O | 100 mg/l |
| Ca SO$_4$ 2 H$_2$O | 60 mg/l |
| NaCl | 8 mg/l |
| KNO$_3$ | 103 mg/l |
| Na NO$_3$ | 689 mg/l |
| Na$_2$ HPO$_4$ | 111 mg/l |
| Conc. H$_2$SO$_4$ | 0.5 l/l |
| FeCl$_3$ | 0.28 mg/l |
| Mn SO$_4$ H$_2$O | 2.2 mg/l |
| Zn SO$_4$ | 0.5 mg/l |
| H$_2$BO$_3$ | 0.5 mg/l |
| Cu SO$_4$ | 0.016 mg/l |
| Na$_2$MoO$_4$ . 2H$_2$O | 0.025 mg/l |
| Ca Cl$_2$ 6H$_2$O | 0.046 mg/l |

Lactose is added to this basal salts culture medium, as sole carbon source, at a level of 6.4 g/l and organisms of the HRI strains of *B. stearothermophilus* (NCIB 11407, NCIB 11408, NCIB 11409, NCIB 11410, NCIB 11411, NCIB 11412, and NCIB 11413) are grown in this medium in batch and continuous culture modes.

Batch culture

An inoculum of 0.002 g (dry weight) of organisms of one HRI strain of *B. stearothermophilus* is added to 1.5 l of batch culture of the above medium in a 2 l. culture container, and grown with aeration at 65° C. with a doubling time of 80 minutes. The yield of organisms obtained is about 0.2 g dry mass cells per liter of medium and the optimum time in the growth curve for cell harvesting to yield maximum specific activity for the enzyme is found to be in the late log phase of the growth cycle. A typical enzyme activity obtained is 20μ moles o-nitrophenyl-β-galacto-pyranoside per minute per mg dry weight of cells.

Continuous culture

Similarly as for batch culture 0.003 g (dry weight) of the HRI strain of *B. stearothermophilus* is inoculated in to 0.75 l of the same medium contained in a 1 l. glass continuous culture container and grown at 65° C. It is found that when the organism is grown under conditions of oxygen limitation the specific activity of the enzyme is decreased, and that enzyme yield increases with dilution rate up to an optimum of 0.1 under oxygen limiting conditions. A yield of 0.4 mg dry weight of cells is obtained per liter of medium.

Similar culture medium and growth conditions, as above, are used to grow strains of *B. stearothermophilus* as an initial indicator of their suitability for derivation of the enzyme, enzyme compositions and enzymatically active whole cell preparations of the invention. Growth in such culture media under such conditions e.g. temperatures around 65° C., is prima facie evidence of the suitability of the organism though ultimate suitability is determined from the thermal stability characteristics of the β-galactosidase isolated from the organism.

EXAMPLE 2

Preparation of enzyme extracts and purified enzyme

A quantity of 20 g dry weight of washed cells of an HRI strain of *B. stearothermophilus*, as prepared in Example 1, is resuspended in 0.15 l of buffer containing 0.15 M potassium chloride and treated with lysozyme by the method of Griffith and Sundaram (J. Bacteriol 1973, 116, 1160) to provide a crude cell extract. The cell-free extract thus obtained is made 25% saturated with respect to ammonium sulphate, the precipitate formed is removed and more ammonium sulphate is added to the supernatant to make a 70% saturated solution. The precipitate thus formed is collected by centrifugation, dissolved in a small quantity of buffer and applied to a Sepharose 6B column (2.6×88 cms). The protein is eluted from the column with 50 mM sodium phosphate buffer, pH7, and the fractions containing β-galactosidase activity are identified by assay and recovered. The pooled enzyme containing fractions are applied to a DEAE-Sepharose CL-6B column (1.6×48 cms) and the protein is eluted with a linear graient of 0–2M sodium chloride. The β-galactosidase containing fractions are pooled and dialysed overnight against 500 mM sodium phosphate buffer, pH7.

An enzyme solution is produced having a specific activity of about 7,500 u/g, where one unit hydrolyses 1μ mole of ONPG per minute at pH7.0 and 65° C.

EXAMPLE 3

Production of whole cell suspension and immobilised whole suspension cell preparations A quantity of 20 g dry weight of cells of an HRI strain of *B. stearothermophilus*, as prepared in Example 1, is suspended in 0.15 l. of 50 mM sodium phosphate buffer, pH7, and a 2:1 solution of toluene-acetone is added at the rate of 1 ml per 10 ml of suspension. The cells are shaken at room temperature for about 5 minutes, and then harvested by centrifugation at 6000 g for 20 minutes in an MSE "Hi Spin 21" centrifuge prior to washing with buffer. The enzymatically active whole cell product obtained is resuspended in buffer to give a cell density of 20.2 mg dry wt/ml. The relation of Harris and Kornberg (Proc. Roy. Soc. Lond. B. 1972, 182, 159) is used to determine the cell density, 0.33 mg. dry wt. of *B. stearothermophilus* corresponding to an absorbance of 1.0 at 680 n.m.

Immobilised cells

Washed cells which have been toluene treated, as above, are resuspended in an equal volume of 50 mM sodium phosphate buffer, pH 7.0, containing acrylamide (200 g/l) and NN'-methylenebisacrylamide (20 g/l). Ammonium persulphate (2 g/l) and TEMED (2 ml/l) are added to this suspension which is then allowed to gel, and the gel is disrupted by forcing through a wire mesh, as described by Hjerten (Arch. Biochem. Biophys. Suppl. 1962, 1, 147). The disrupted gel is freeze-dried to provide a stock of enzymatically active immobilised whole cell preparation.

EXAMPLE 4

Assay and characterisation of β-galactosidase

The purified enzyme and enzymatically active whole cell preparations, as prepared in Examples 2 and 3, are assayed under various conditions. The results obtained are characteristic of the HRI enzyme, though, without prejudice, it is believed that these results are representative of the characteristics of other novel β-galactosidases of the invention. The general techniques used for assay are as follows:

use of o-nitrophenyl-β-D-galactopyranoside (ONPG) as substrate

The assay used is based on that of Lederberg (J. Bacteriol. 1950, 60, 381), using an assay mixture comprising 2.8 ml of 50 mM sodium phosphate, pH 7.0, and 0.1 ml of 68 mM ONPG. 0.1 ml aliquots of both purified enzyme and toluene-treated cell suspension, and 10 mg. amounts in 2.9 ml of buffer of freeze dried immobilised whole cell preparation are used for the assays. Assays are carried out at incubation temperature of 65° C. and after the appropriate time interval the reactions are halted by addition of 3 ml aliquots of 0.5 M sodium bicarbonate to each reaction mixture and immediate cooling in an ice bath. The absorbance of the resultant solutions is measured at 410 nm using a Perkin-Elmer 124 double beam spectrophotometer. In the case of whole cell suspensions the assay tubes are centrifuged and in the case of the immobilised cells the mixtures are filtered, to remove cells and polyacrylamide gel respectively prior to measurement of the absorbance.

During experiments to determine the pH optimum of the enzyme, the usual sodium phosphate buffer was replaced by McIlvaines citricacid-phosphate buffer (elving, Markowitz and Rosenthal, Analyt. Chem. 1956, 28, 1179) at appropriate pHs.

Use of lactose as substrate

The assay mixture used comprises 0.9 ml of 50 mM sodium phosphate buffer, pH 7.0, 4 ml of lactose (4 g in 100 ml of phosphate buffer), to which 0.1 ml of purified enzyme or cell suspension or 10 mg of gel entrapped cell preparation is added. The reaction mixtures are incubated for 15 minutes at 65° C., reactions are halted by addition of 4.2% perchloric acid and the solutions are centrifuged. Aliquots of the supernatant solutions are assayed for glucose or galactose.

Glucose is estimated by a modification of the method of Trinder (Ann. Clin. Biochem. 1969 6, 24). 1 ml aliquots of the supernatant solutions are assayed by addition to a mixture comprising 1 ml of 0.2% phenol and 3 ml of colour reagent (75 ml 4% (w/v) disodium hydrogen orthophosphate, 225 ml of water, 6 mg of glucose oxidase (Boehringer Corp. Ltd.), 0.15 ml peroxidase (Boehringer Corp. Ltd.), 100 mg of 4-aminophenazone and 300 mg of sodium azide) followed by incubation at 37° C. for 10 minutes and absorbance measurement at 515 nm.

Galactose is estimated as follows: a sample (e.g. 0.2 ml) containing not more than 200 μg/ml of galactose is mixed with 2.5 ml of buffer (4.8 g $Na_2HPO_4$, 0.86g $NaH_2PO_4$ and 0.2 g $MgSO_4\ 7H_2O$ per 200 ml of $H_2O$) and 0.1 ml of 10 mg/ml of NAD solution and the absorbance is measured at 340 nm. 0.02 ml of galactose dehydrogenase (Boehringer Corp. Ltd.) is added, the solutions incubated at 37° C. for 30 minutes and the absorbance again measured at 340 nm.

Thermostability measurements

To determine the thermostability of the enzyme preparations, 0.5 ml aliquots of purified enzyme (2.7 mg/ml of protein), or cell suspension, or 10 mg amounts in 2.9 ml of 50 mM sodium buffer of the freeze-dried gel immobilised preparation, are heated in sealed tubes at appropriate temperatures for the requisite periods of time. After such heat treatment the residual β-galactosidase activity is assayed using ONPG as substrate. 0.1 ml aliquots of purified enzyme or cell suspension are removed from the tubes and assayed for enzyme activity. In the case of immobilised whole cells the residual β-galactosidase activity is assayed by adding ONPG (0.1 ml) to the reaction mixtures and following the usual procedure detailed previously for use of ONPG as substrate. This procedure for thermostability measurement may be used to determine whether enzyme from strains of B. stearothermophilus are novel enzymes according to the present invention.

Lactose determination

The lactose concentration of milk and milk products is determined by the method of Nickerson et al (J. Dairy Sci. 1976, 59, 386).

(a) Effect of temperature on enzyme activity

Figure 1:
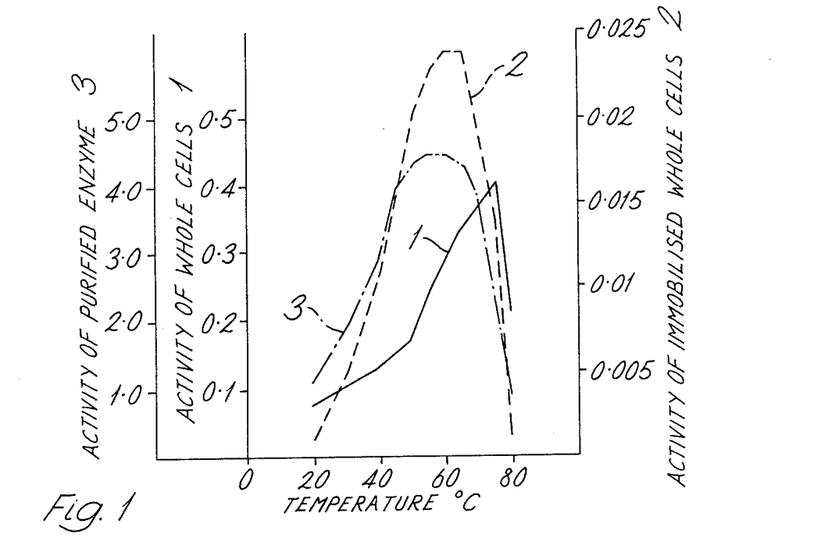
FIG. 1 is a graph of $\beta$-galactosidase activity of purified enzyme, whole cells and immobilised whose cells at various temperatures.

The effect of temperature on the relative activity of β-galactosidase in whole cell suspension preparation (curve 1), entrapped whole cell preparation (curve 2) and purified enzyme extract (curve 3) is shown in FIG. 1, the temperature for optimum activity being 75°, 65° and 60° C. respectively. In FIG. 1 the activity is given in terms of μ moles of nitrophenol formed per minute per mg of protein or per mg dry weight of cells and the differing scales used are marked in accordance with their corresponding curves.

From the data obtained the activation energies are determined and found to be closely similar for the purified enzyme and the whole cell preparation (69.2 k cal/mol. and 61.8 k cal/mol respectively), though somewhat higher (155.7 k cal/mol) for the entrapped whole cell preparation. This latter observation is believed to be caused by the effect of diffusion processes within the gel matrix.

(b) Effect of pH on enzyme activity

Figure 2:
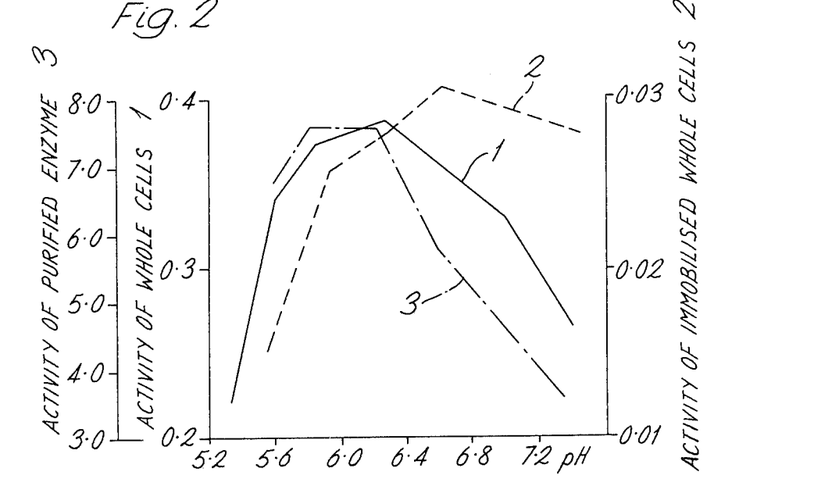
FIG. 2 is a similar graph of $\beta$-galactosidase activity at various pHs.

The pH-activity profiles for the β-galactosidase activities of whole cell suspension preparation (curve 1), entrapped whole cell preparation (curve 2) and purified enzyme extract (curve 3) are shown in FIG. 2. The pH optima are 6.2, 6.6 and 6.0 respectively, though all three sources of enzyme show activity over a wide range of pH. The units and arrangement of FIG. 2 are similar to those of FIG. 1.

(c) Stability of enzyme on prolonged incubation

The results obtained for enzyme activity after incubation at various temperatures is given below in Table 2.

TABLE 2

Thermostability of β-galactosidase from the HRI strains of B. stearothermophilus using whole cells, purified enzyme and immobilised whole cells as enzyme sources

| Temperature °C. | Half-life (Mins) of β-galactosidase Activity | | |
|---|---|---|---|
| | Whole cells | Purified Enzyme | Immobilized Whole cells |
| 55 | 635 | No inactivation after 90 mins | 800 |
| 60 | 355 | 450 | 530 |
| 65 | 190 | 85 | 230 |
| 70 | 125 | 20 | 25 |

The results obtained evidence the extremely good thermal stability of the β-galactosidase in all three sources at temperatures of 55° and 60° C. At higher temperatures the enzyme activity of the whole cell suspension preparation becomes markedly more stable than that of the purified enzyme.

(d) Michaelis constant for ONPG and lactose

The Michaelis constants (Km) with ONPG as substrate for the β-galactosidase activity of whole cell suspension, purified enzyme and entrapped whole cell preparation are found to be $3.8 \times 10^{-4}M$, $4.3 \times 10^{-4}M$ and $2.6 \times 10^{-4}M$ respectively.

With lactose as substrate, however, the Kms for the β-galactosidase of whole cell suspension and entrapped whole cell preparation are found to be $1.18 \times 10^{-2}M$ and $9.52 \times 10^{-3}M$ respectively whereas that for purified enzyme extract is found to be $2.06 \times 10^{-3}M$.

(e) Inhibition of enzyme by glucose and galactose

Addition of either glucose or galactose to the assay mixtures inhibits enzyme activity from all sources with both ONPG and lactose as substrate, galactose inhibition being the more marked. For example, the inhibition constant (Ki) for galactose with lactose as substrate using whole cell suspension is $2.3 \times 10^{-2}M$, for purified enzyme $2.0 \times 10^{-2}M$ and for entrapped whole cell preparation $2.6 \times 10^{-2}M$. The Ki's for glucose, with lactose as substrate are much higher, being $2.2 \times 10^{-1}M$ for whole cell suspension, $1.3 \times 10^{-1}M$ for purified enzyme and $2.6 \times 10^{-1}$ for entrapped whole cell preparation.

(f) Effect of divalent cations on enzyme activity

The effect on enzyme activity of adding certain divalent cations, cysteine and protein (in the form of bovine serum albumin) is shown in Table 3 below. Enzyme activity is determined using ONPG as substrate, all additions being made to a final concentration of 10 mM with the exception of bovine serum albumin which is added to a final concentration of 1.5 mg/ml.

TABLE 3

Effect of certain divalent cations and etc. on
β-galactosidase activity using whole cell suspension,
purified enzyme, and immobilised whole cell preparation
of *B. stearothermophilus* HRI

| Addition | Whole Cells | | Purified Enzyme | | Immobilised Whole Cells | |
|---|---|---|---|---|---|---|
| | Specific Activity mole/min/ mg cells | % Activity | Specific Activity mole/min/ mg Prot. | % Activity | Specific Activity mole/min/ mg/Gel | % Activity |
| None | 0.427 | 100 | 7.002 | 100 | 0.032 | 100 |
| CaCl$_2$ | 0.426 | 99.8 | 6.690 | 95.5 | 0.032 | 100 |
| MgCl$_2$ | 0.512 | 119.9 | 11.114 | 158.7 | 0.041 | 128.1 |
| MgSO$_4$ | 0.512 | 119.9 | 11.110 | 158.7 | 0.042 | 131.3 |
| FeSO$_4$ | 0.519 | 121.5 | 11.556 | 165.0 | 0.038 | 118.8 |
| CuSO$_4$ | 0.062 | 14.5 | 0.548 | 7.8 | 0.001 | 3.1 |
| Cysteine | 0.443 | 103.7 | 6.866 | 98.1 | 0.035 | 109.4 |
| Bovine Serum Albumin | 0.436 | 102.1 | 7.804 | 111.5 | 0.032 | 100 |

$Mg^{2+}$ and $Fe^{2+}$ act as activators for all enzyme sources, $Cu^{2+}$ is a powerful inhibitor, cysteine produces little or no effect and there is slight activation of the purified enzyme in the presence of protein. In all cases where significant activation is achieved the effect is greatest for the purified enzyme.

(g) Effect of β-galactosidase on a range of substrates

The β-galactosidase of HRI strains of *B. stearothermophilus* is found to be active for hydrolysing lactose in whole milk, skim milk, whey, demineralised whey and permeate from whey after ultrafiltration.

Figure 3:
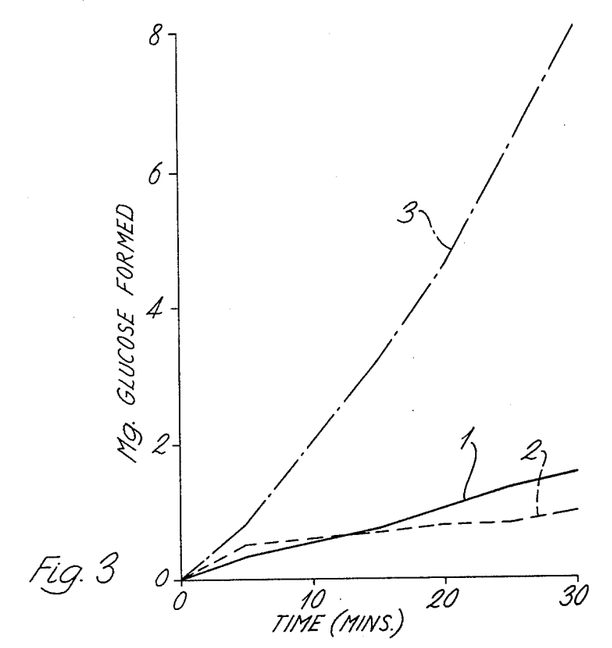
FIG. 3 is a graph showing the $\beta$-galactosidase activities of purified enzyme, whole cells and immobilised whole cells for lactose hydrolysis in demineralised whey.

With reference to FIG. 3, enzyme from all three sources (whole cell suspension—curve 1, immobilised whole cell preparation—curve 2 and purified enzyme—curve 3) is active in hydrolysing the lactose of demineralised whey. FIG. 3 is given in terms of mg of glucose produced (y axis) against time in minutes (x axis). Thus the conversion of lactose after 30 minutes at 65° C. is about 7.5% for whole cell suspension, 40% for purified enzyme and 5% for immobilised whole cell preparation.

Figure 4:
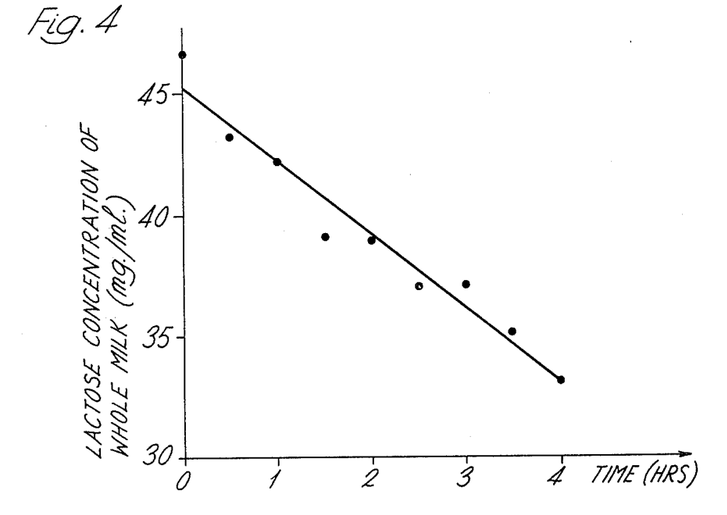
FIG. 4 is a graph showing the $\beta$-galactosidase activity of purified enzyme for the hydrolysis of lactose in whole milk.

Also, the action of purified enzyme on the hydrolysis of lactose in whole milk is shown in FIG. 4, which is given in terms of lactose content (y axis; mg/ml) of the milk against time (x axis; hours). After 4 hours at 65° C. about 30% hydrolysis is achieved by only 14 units of enzyme in 20 ml of whole milk.

EXAMPLE 5

Production assay and characterisation of ion-exchange support material—immobilised whole cell preparation Cells of the HRI strain of *B. stearothermophilus* are grown under continuous culture conditions as described in Example 1. The cells are then immobilised by attachment to DEAE-cellulose (Vistec D.1. cellulose media, S. grade Koch-Light Laboratories Limited), amino-ethyl cellulose (Sigma Chemical Company Limited), DEAE-Sephadex A50 (Pharmacia) and DEAE-Sepharose CL6B (Pharmacia), the same immobilisation procedure being employed in each case. The procedure used is described in detail below for DEAE-cellulose.

Dry DEAE-cellulose is stirred into 15 volumes of 0.5 N HCl, allowed to stand for 30 minutes, and the supernatant removed by suction filtration using a Buchner funnel. The cellulose is then washed with distilled water until the pH of the washings is between 4.0 and 8.0. The washed media is stirred into 15 volumes of 0.5 N NaOH and, after 30 minutes, the alkali is removed and the cellulose washed with water until the washings are at neutral pH. The washed DEAE-cellulose is resuspended in 50 mM sodium phosphate buffer, pH 7.0, and glutaraldehyde (25% w/v aqueous solution) added to give a final concentration of 1% w/v. After stirring for 2 hours at room temperature, the cellulose derivative is recovered by filtration, and the excess glutaraldehyde removed by washing with the sodium phosphate buffer (50 mM, pH 7). The DEAE-cellulose is resuspended in buffer and an equal volume of a suspension in the same buffer of cells of *B. stearothermophilus* (40 mg dry mass per ml) as prepared above, is added. The suspension is stirred for a further 2 hours at room temperature and the immobilised cells are recovered by filtration. The immobilised cells are washed with sodium phosphate buffer containing 0.5 M NaCl to remove non-covalently bound cells, followed by washing with buffer containing no added NaCl.

Comparison of beta-galactosidase activity of *B. stearothermophilus* cells attached to various ion-exchange supports Four jacketed chromatography columns (A. Gallenkamp and Company Limited) are filled with cells immobilised as described above, one column for each of the different kinds of ion-exchange support material used. A 5% w/v lactose solution in 50 mM phosphate buffer, pH 7.0, is eluted upwards through the columns. The columns are thermostatted at 60° C., and samples of the eluate are assayed for glucosegalactose content at regular intervals.

Figure 5:
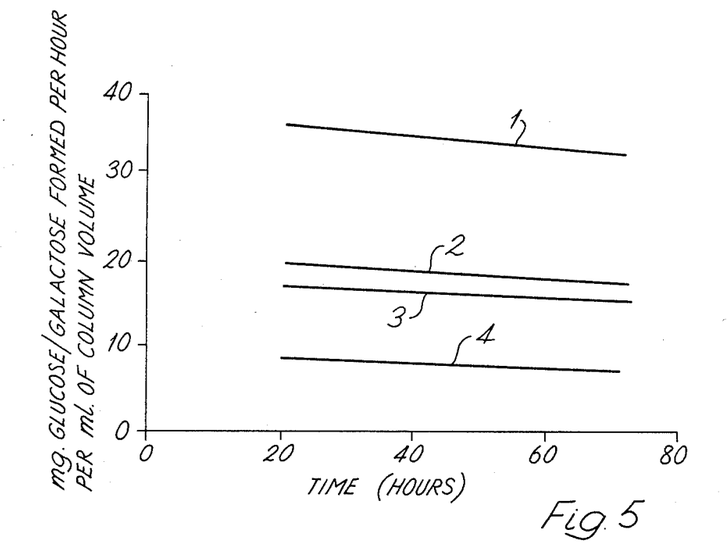
FIG. 5 is a graph showing the $\beta$-galactosidase activity of cells immobilised on various cellulosic ion-exchange support materials.

The results obtained are given in the accompanying diagram, FIG. 5, the extent of hydrolysis being expressed in terms of mg of glucose/galactose formed per hour per ml of column volume. The results for the DEAE-cellulose, DEAE-Sephadex A50, DEAE-Sepharose CL6B and amino-ethyl cellulose supports are given by lines 1, 2, 3 and 4 respectively. By far the greatest activity is observed with the column packed with cells immobilised on DEAE-cellulose. This result, however, does not reflect the total ion exchange capacity of the gels, and although amino-ethyl cellulose has the lowest capacity (0.3 meq. per g) both DEAE-Sephadex A50 (3.5 m eq. per g) and DEAE-Sepharose (approximately 2.2 m eq. per g at pH 7) both have higher capacities than DEAE-cellulose (1 m eq. per g).

In view of the outstanding properties of glutaraldehyde-treated DEAE-cellulose immobilised cells as compared with cells immobilised on other supports further investigation and characterisation is restricted to this material. First of all, however, the binding capacity of glutaraldehyde-treated DEAE-cellulose for whole cells of B. stearothermophilus and the activity of the beta-galactosidase of these immobilised cells is investigated. The amount of cells bound to the glutaraldehyde-treated DEAE-cellulose is estimated by determining the dry mass of cells remaining after attachment to the matrix, and comparing that with the dry mass of the original cell suspension, the difference being taken as the dry mass of cells which bind to the cellulose material. These investigations show that the weight of cells bound appears to vary with treatment, but on average between 2 and 4 mg dry mass of cells are bound per g of DEAE-cellulose. This is lower than is found for DEAE-cellulose which has not been treated with glutaraldehyde (about 4–8 mg dry mass of cells per g of support) suggesting that not all the available reactive sites of the DEAE-cellulose are occupied by glutaraldehyde molecules.

The beta-galactosidase activity of cells immobilised on DEAE-cellulose is assayed using ONPG as substrate under standard conditions, as in Example 4, and that for glutaraldehyde-treated DEAE-cellulose support appears to be higher than the activity remaining in cells absorbed on to untreated DEAE-cellulose (about 7.7 and 3.5 units per milligram dry mass of cells immobilised respectively). The beta-galactosidase activity of the glutaraldehyde-treated gel bed is approximately 22 units per g of support.

Effect of flow rate of substrate through columns

Figure 6:
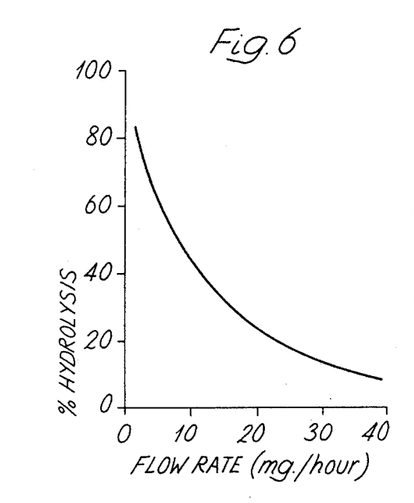
FIG. 6 is a graph of $\beta$-galactosidase activity of DEAE-cellulose immobilised cells against substrate flow rate.

A 5% w/v lactose solution in 50 mM phosphate buffer, pH 7.0, is eluted at various flow rates through columns maintained at 60° C. containing glutaraldehyde-treated DEAE-cellulose immobilised cells (bed volumes 66.5 ml). Samples are collected and the lactose concentration of the eluate is determined, and the results are given in the accompanying diagram, FIG. 6. The results show that by varying the flow rate, greater than 80% hydrolysis of the lactose solution can be achieved.

The effect of pH on the activity of Beta-galactosidase of immobilised cells

Columns are packed with cells immobilised on glutaraldehyde-treated DEAE-cellulose (bed volume 73 ml) and 5% w/v lactose solution in sodium phosphate buffers of ionic strength 0.1 and various pH's are eluted through the beds at a flow rate of approximately 19 ml per hour. Eluate samples are removed at regular intervals over several days and assayed to determine the lactose concentration present. Half lives are estimated by regression analysis of graphs of lactose converted per hour against time. The results obtained are given below in Table 4.

TABLE 4

| Apparent half-lives of β-galactosidase activity of immobilised cells at different pH's | |
|---|---|
| pH | Half-life (Days) |
| 5.5 | 1.5* |
| 6.0 | 4.5 |
| 6.6 | 10 |
| 7.0 | 16.5 |

TABLE 4-continued

| Apparent half-lives of β-galactosidase activity of immobilised cells at different pH's | |
|---|---|
| pH | Half-life (Days) |
| 7.4 | 33 |

*at this pH the lactose solution was buffered with McIlvaines citric acid-phosphate buffer.

Figure 7:
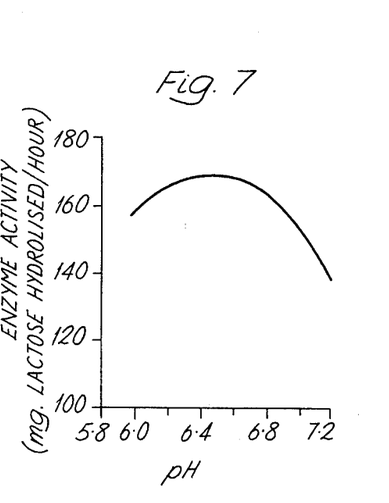
FIG. 7 is a graph showing the $\beta$-galactosidase activity of DEAE-cellulose immobilised cells against pH.

Also the results obtained for β-galactosidase activity at the various pH's are given in the accompanying diagram, FIG. 7. Thus the thermal stability of the product appears to increase with increasing pH though the optimum pH for activity appears to be about 6.4.

Effect of temperature on the beta-galactosidase activity of immobilised cells

Figure 8A:
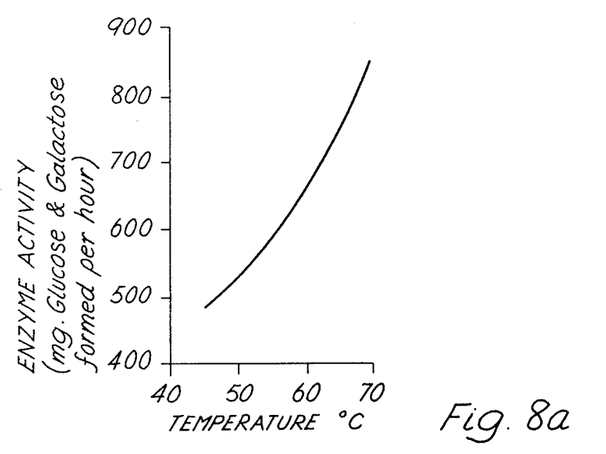
FIG. 8 are graphs showing $\beta$-galactosidase activity of DEAE-cellulose immobilised cells against temperature.
Figure 8B:
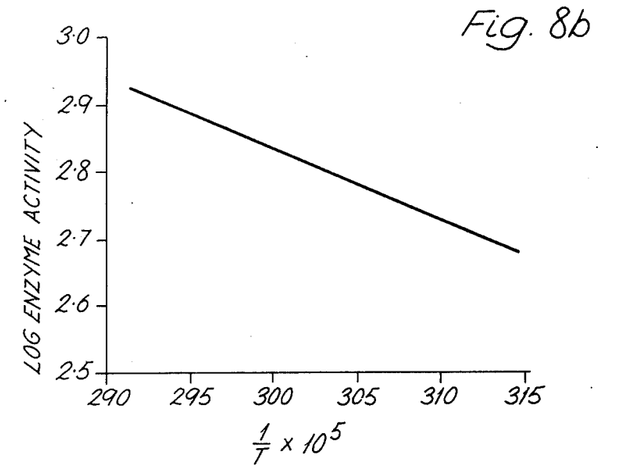

A 5% w/v solution of lactose in 50 mM phosphate buffer, pH 7.0, is eluted through columns containing glutaraldehyde-treated DEAE-cellulose immobilised cells (bed volume 58.5 ml). The columns are maintained at different temperatures and activity of the enzyme is determined by assaying the glucose and galactose concentrations in the eluate stream over a period of up to 4 days. The results obtained are given in the accompanying diagram, FIG. 8(a) and an Arrhenius plot of the beta-galactosidase activity is calculated from these results and is given in FIG. 8(b). The half lives of beta-galactosidase activity of immobilised cells are also determined and the results are given in Table 5 below. Half lives are estimated by regression analysis of the results given in FIG. 8(a).

TABLE 5

| Apparent half-lives of β-galactosidase activity of immobilised cells at different temperatures | |
|---|---|
| Temperature (°C.) | Half-life (Days) |
| 45 | 68.5 |
| 50 | 45 |
| 55 | 19 |
| 60 | 15 |
| 65 | 8.5 |
| 70 | 3.5 |

Figure 9:
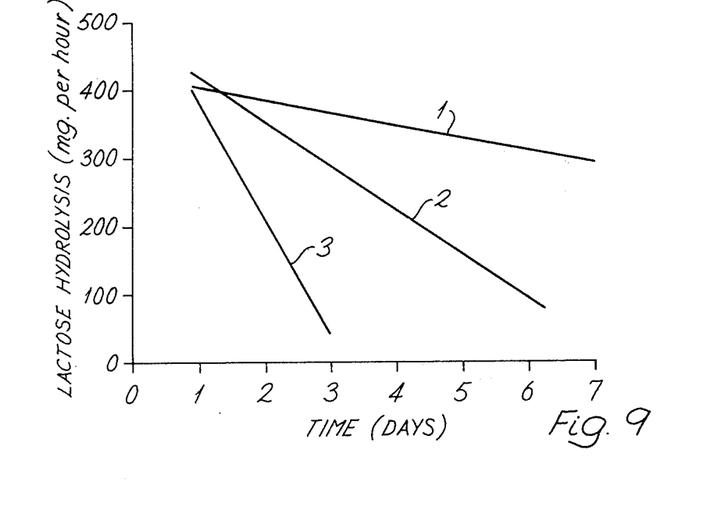
FIG. 9 is a graph showing $\beta$-galactosidase activity of DEAE-cellulose immobilised cells against ionic strength.

Effect of ionic strength on the beta-galactosidase activity of immobilised cells Lactose solutions (5% w/v) are prepared in phosphate buffers (pH 7.0) of differing ionic strengths, and the activity half lives of the immobilised cells are determined, the results being given in the accompanying diagram FIG. 9. 5% w/v solutions of lactose in sodium phosphate buffers, pH 7.0 and ionic strengths of 0.1 (line 1); 0.5 (line 2); and 0.85 (line 3); are eluted through columns containing glutaraldehyde-treated DEAE-cellulose immobilised cells (bed volume 66.5 ml) at flow rates of approximately 20 ml per hour. The column temperatures are maintained at 60° C. and samples of the eluate are removed at intervals and assayed for lactose content. The activity of the enzyme is expressed as the amount of lactose hydrolysed per hour, and half lives are determined by regression analysis assuming linear decay of the enzyme activity with time.

Activity of the beta-galactosidase of immobilised cells on various substrates

Figure 10:
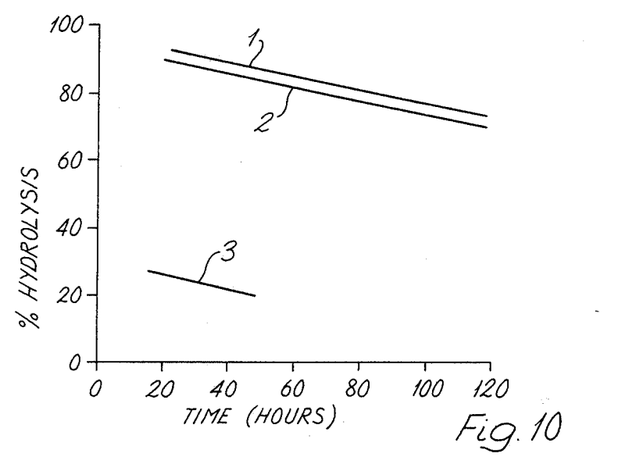
FIG. 10 is a graph showing $\beta$-galactosidase activity of DEAE-cellulose immobilised cells for various lactose substrates.

Pure lactose, demineralised whey and skimmed milk are used as lactose sources for the glutaraldehyde-treated DEAE-cellulose immobilised cells and the results obtained are given in the accompanying diagram, FIG. 10. A 5% solution of lactose in 50 mM phosphate buffer, pH 7.0 (line 1); a solution of demineralised, ultrafiltered whey containing 48.95 mg per ml of lactose and at pH 6.55 (line 2); and skim milk containing 48.50 mg per ml of lactose and at pH 6.86 (line 3), are eluted through a column maintained at 60° C. containing glutaraldehyde-treated DEAE-cellulose immobilised cells (bed volume 41 ml). The flow rates are 28.3, 29.5 and 29.5 ml per hour respectively for the three substrates. The amount of glucose/galactose formed in samples of eluate is determined and the percentage hydrolysis calculated.

We claim:

1. A beta-galactosidase in substantially purified form having an activity half life of at least 5 hours at 55° C., at least 3 hours at 60° C., at least 1 hour at 65° C. and at least 10 minutes at 70° C., as measured using ONPG as substrate, said enzyme being derived from a strain of *Bacillus Stearothermophilus* identified as NCIB 11407, NCIB 11408, NCIB 11409, NCIB 11410, NCIB 11411, NCIB 11412 or NCIB 11413.

2. An immobilised beta-galactosidase composition comprising a beta-galactosidase enzyme according to claim 1, in which the enzyme is immobilized with a solid phase material.

3. An immobilised enzymically active, whole cell preparation of bacteria of species *Bacillus Stearothermophilus* which contains a beta-galactosidase according to claim 1.

4. An immobilised enzymically active whole cell preparation according to claim 3, in which the cells are immobilised on or with an ion-exchange support material.

5. An immobilised enzymically active whole cell preparation according to claim 4, in which the ion-exchange support is selected from the group consisting of aminoethyl cellulose and diethylaminoethyl-containing ion exchange supports.

6. An immobilised enzymically active whole cell preparation according to claims 4 or 5 having an enzyme activity half life for lactose hydrolysis of at least 7 days at 60° C. and pH 7.

7. A process for the hydrolysis of lactose to a product comprising glucose and galactose, in which lactose is contacted with a product comprising beta-galactosidase and selected from the group consisting of (1) substantially purified beta-galactosidase enzyme, (2) immobilised cell composition containing beta-galactosidase enzyme, and (3) enzymically active whole cell preparation, containing beta-galactosidase enzyme, wherein said beta-galactosidase enzyme has an activity half life of at least 5 hours at 55° C., at least 3 hours at 60° C., at least 1 hour at 65° C. and at least 10 minutes at 70° C. when in substantially purified form as measured using ONPG as substrate, said enzyme being derived from a strain of *Bacillus stearothermophilus* identified as NCIB 11407, NCIB 11408, NCIB 11409, NCIB 11410, NCIB 11411, NCIB 11412 or NCIB 11413; and wherein said immobilised cell composition or enzymically active whole cell preparation is derived from a strain of *Bacillus stearothermophilus* identified as NCIB 11407, NCIB 11408, NCIB 11409, NCIB 11410, NCIB 11411, NCIB 11412 or NCIB 11413.

8. A process according to claim 7, which is carried out at a temperature of at least 55° C.

9. A process according to claims 7 or 8, in which said lactose which is contacted with said product containing beta-galactosidase is in the form of whey or other lactose - containing milk product.

* * * * *